United States Patent [19]

Mueller et al.

[11] Patent Number: 4,692,552

[45] Date of Patent: Sep. 8, 1987

[54] PROTEASE INHIBITORS

[75] Inventors: Richard A. Mueller, Glencoe; Richard A. Partis, Evanston, both of Ill.

[73] Assignee: G. D. Searle & Co., Chicago, Ill.

[21] Appl. No.: 831,238

[22] Filed: Feb. 18, 1986

Related U.S. Application Data

[63] Continuation of Ser. No. 664,447, Oct. 24, 1984, which is a continuation of Ser. No. 492,842, May 9, 1983, Pat. No. 4,499,295.

[51] Int. Cl.$^4$ .................. C07C 65/04; C07C 69/88
[52] U.S. Cl. ................... 562/475; 562/473; 560/67; 560/64
[58] Field of Search .................. 560/64, 67; 562/473, 562/475

[56] References Cited

PUBLICATIONS

McCoubrey, A. et al, J. Pharm. Pharmacol., 22 (5) 333-7, 1970.

Yahagi, N., Sogo Shihensho Nenpo (Tokyo Daigaler Kogahubu), 1978.

Primary Examiner—Paul J. Killos
Attorney, Agent, or Firm—Mary Jo Kanady; Paul D. Matukaitis

[57] ABSTRACT

This invention relates to methods of preventing or reducing the degradation of elastin and other proteins and thereby preventing or retarding the disease states caused by said degradation by administering compounds of the formula:

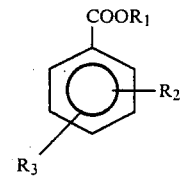

or their pharmacologically acceptable salts.

2 Claims, No Drawings

PROTEASE INHIBITORS

This is a continuation of application Ser. No. 664,447, filed Oct. 24, 1984, which is a continuation of 492,842 filed May 9, 1983, now U.S. Pat. No. 4,499,295.

BACKGROUND OF THE INVENTION (a) Field of the Invention

This invention in its broadest aspect relates to protease inhibitors. In one aspect, the invention relates to certain novel methods useful in preventing or treating disease states caused by the degradative action of proteases on mammalian elastin and other proteins by administration of effective amounts of compounds of Formula II. A preferred method relates to the inhibition of the proteases elastase and cathepsin G. In other aspect, it relates to compounds of Formula I which are useful in preventing or treating disease states caused by the degradative action of proteases on mammalian elastin and other proteins.

Elastin is the functional protein component of elastic fiber tissues, a component of connective tissues. Elastic tissue is relatively rich in elastin and has a distinct rubber-like property. Most specifically, the ligamentum nuchae and the vocal cords, the vertebral ligamenta flava, the aorta, and the pulmonary arteries of some mammals are considered elastic tissues. Elastic cartilaginous tissues such as those present in the ear and epiglottis are a specialized form of elastic tissue. Lung, bronchi and skin also contain elastin and are considered elastic tissue. Sandberg, et al., *New England Journal of Medicine*, Mar. 5, 1981, 566–579.

Elastase is an elastinolytic enzyme which causes degradation and fragmentation of elastic fibers by its catalytic activity against elastin. Elastases originate from a number of sources and can be found in microorganisms, snake venoms and a number of mammalian cells and tissues including pancreas, polymorphonuclear leukocytes, and macrophages. In a normally functioning mammal, elastase is required for turnover of damaged cells and the digestion of certain invading bacteria. This invention in particular relates to the class of elastases known as the Serine Proteases.

Excessive elastin degradation has been associated with pulmonary emphysema, adult respiratory-distress syndrome, arthritis, atherosclerosis, certain skin diseases, and certain inflammatory processes leading to localized protein breakdown. Werb, et al., *Journal of Investigative Dermatology*, 79:154S–159S, (1982); Rinaldo, et al, *New England Journal of Medicine*, 306: 900–909, (1982). By inhibiting elastase therefore it is possible to mediate, eliminate or treat a wide variety of disease conditions.

A number of inhibitors of elastase are known. Peptide chloromethyl ketones have been shown to be irreversible inhibitors of elastase. But difficulties must be considered when the in vivo use of peptide chloromethyl ketones is contemplated. The compounds are electrophiles and can react with good nucleophiles such as the thiol groups of glutathione and various proteins. During any long term treatment with these inhibitors, such non-specific alkylation could lead to the introduction of new antigenetic determinants and an autoimmune response and/or could behave similarly to the known nitrogen mustards, etc. Peptides containing aza-amino acid residues (aza peptides) are another class of inhibitors. The effectiveness of aza-peptides as elastase inhibitors depends on the rate of acylation, which in most cases is instantaneous, and also on the rate of deacylation. As such, these compounds while useful tools in studying the in vitro properties of elastase are still largely unsuitable for in vivo use.

(b) Information Disclosure

The treatment of certain disease states by inhibitors of elastase is known as described above. One compound useful in practicing the method of the invention is previously known as a dye agent or agent for improving textile fibers. See Chem Abstracts: 3285-9 (1937).

SUMMARY OF THE INVENTION

The invention relates to compounds of the formula:

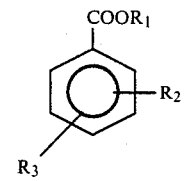

I wherein $R_1$ is:
  (a) hydrogen; or
  (b) alkyl or 1 to 6 carbon atoms, inclusive;
wherein $R_2$ is:
  (a) hydroxy; or
  (b) alkoxy of 1 to 6 carbon atoms, inclusive;
wherein $R_3$ is
  (a) —CH(OH)$R_4$;
  (b) —CH$_2$R$_4$; or
  (c) —CH=CHR$_4$;
wherein $R_4$ is alkyl of 13 to 25 carbon atoms inclusive and the pharmacologically acceptable base addition salts thereof.

This invention also relates to a method of preventing or reducing the degradation of natural tissues in mammals by proteases which comprises administering an effective amount compound of the formula:

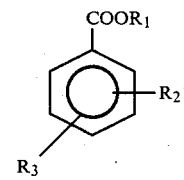

II wherein $R_1$ is:
  (a) hydrogen; or
  (b) alkyl of 1 to 6 carbon atoms, inclusive;
wherein $R_2$ is:
  (a) hydroxy; or
  (b) alkoxy of 1 to 6 carbon atoms, inclusive;
wherein $R_3$ is:
  (a) —C(O)R$_4$;
  (b) —CH(OH)R$_4$;
  (c) —CH$_2$R$_4$; or
  (d) —CH=CHR$_4$;
wherein $R_4$ is alkyl of 13 to 25 carbon atoms inclusive and the pharmacologically acceptable base addition salts thereof. A preferred method relates to the inhibition of the proteases elastase and cathepsin G.

Examples of alkyl of 1 to 6 carbon atoms inclusive are methyl, ethyl, propyl, butyl, pentyl, hexyl and the isomeric forms thereof.

Examples of alkoxy of 1 to 6 carbon atoms, inclusive, are methoxy, ethoxy, propoxy, butoxy, pentoxy, hexoxy and the isomeric forms thereof.

Examples of alkyl of 13 to 25 carbon atoms inclusive are dodecanes, dodecenes, hexadecanes, hexadecenes, pentadecanes, pentadecenes, eicosodecanes, eicosodecenes and the like, as well as their branched chain isomers.

Salts of the acid forms of these compounds ($R_1$=H or $R_2$=OH) can be prepared by neutralization with the appropriate amount of an inorganic or organic base such as sodium hydroxide, potassium hydroxide, calcium hydroxide, magnesium hydroxide, ammonia, trialkylamine, dialkylamine, monoalkylamine, dibasic amino acids, sodium acetate, potassium benzoate, triethanol amine and like bases.

The compounds useful in practicing the method of the invention are inhibitors of leucocyte elastase and cathepsin G. Since elastase is involved in the breakdown of elastin and subsequently involved in a number of disease states, a compound which blocks the action of elastase will be useful in the management, treatment and prevention of such diseases. Elastase, in addition to degrading elastin, also will hydrolyse methoxysuccinyl-ala-ala-pro-val-nitroanalide (MSN), a highly selective synthetic substance. Kakajima, K., et al., *J. Biol. Chem.*, 254, 4027 (1979). This is useful in measuring inhibition of elastase because the hydrolysis of MSN is easily quantitated by measuring the release of p-nitroaniline spectrophotometrically. Therefore, the degree of elastase inhibition can be readily measured by noting the rate of inhibition of the hydrolysis of MSN. The compounds of the invention are therefore tested in vitro as follows. The rate of hydrolysis of methoxysuccinyl-ala-ala-pro-val-nitroanalide by human leukocyte elastase is monitored spectrophotometrically in the presence and absence of test compound. The inhibition of the eznymatic reaction by 20% or more is taken as positive inhibition. $IC_{50}$ values are then determined.

The following procedure is used to test the compounds in vivo (collagen-induced rat arthritis model). The method is based on that of Trentham, D. E. Townes, A. S. and Kang, A. H. in *J. Exp. Med.* 146, 857–968 and results are evaluated thereby.

Inbred female Wistar rats (200-230 G) were randomly assigned to 3 groups of 30 animals each. Arthritis was induced by intradermal injection of bovine nasal septum Type II collagen in incomplete Freunds adjuvant.

Drug treatment was oral, once daily in 0.5 ml carboxymethyl cellulose from day 0 until sacrifice:
Group I: Test compound 50–100 mg/kg/day
Group 2: Phenylbutazone 40 mg/kg/day (positive control)
Group 3: 1% V/V carboxymethyl cellulose (negative control)

(1) Physical measurements of hind paws were made for (a) swelling across plantar region; (b) malleolar thickening; (c) extensibility of ankle joint. Results were subject to systematic statistical evaluation.

(2) Histological examination of hind paws were made in groups of 5 animals sacrificed at days 7, 14, 21 and 28. Sections were taken at 3 levels through each foot and examined for indication of disease progression.

During periods of active rheumatoid arthritis, vast numbers of human neutrophils are attracted to diseased joints where they engage in phagocytosis of locally generated immune complexes and tissue debris. During the process, enzymes (primarily elastase and cathepsin G) are released into the joint spaces. Elastase has the capacity in this situation to degrade synovial cartilage and collagen and contribute to joint destruction in a synergistic process with cathepsin G. Cathepsin G also causes conversion of angiotensin I to angiotensin II which is associated with inflammatory processes, Reilley, C. F., et al., *J. Biol. Chem.*, 257, 8619 (1982) and angiotensinogen to angiotensin II, Tonnesen, M. G., et al., *J. Clin. Invest.*, 69, 25 (1982). Natural elastase inhibitors (macro molecules such as in $\alpha_1$-proteinase inhibitor) already exist in normal serum and synovial fluid and may prevent precipitous joint destruction. Oxidation of the natural inhibitor (to the sulfoxide form) renders this material inactive. Wong, P. S. and J. Travis, *Biochem Biophys. Res. Commun.*, 96, 1449 (1980). Exogenous smaller molecular weight inhibitors of the invention can gain access to the micro-environments within the joint space not accessible to the natural inhibitors due to their molecular size, oxidation, charge repulsion or lipid solubility, and thereby inhibit or prevent further elastase-related destruction. In addition, pulmonary emphysema is a disease characterized by a progressive uninhibited proteolysis of lung tissue by enzymes such as elastase which in this case are released from leukocytes. People who are homozygotes in an $\alpha_1$-antitrypsin deficiency are predisposed to the disease. See, e.g., Turimo, et al., *Amer. J. Med.*, Vol 57, pp. 493–503 (1974). The compounds of the invention could also be used to prevent the further proteolysis of lung tissue. Again, the ability of the compounds to inhibit cathepsin G is desirable, since the combination of elastase and cathepsin G has been reported to be five times as efficient at degrading elastin as is elastase alone. Boudier, C., et al., *J. Biol. Chem.* 256, 10256 (1981). In a like manner, adult respiratory-distress syndrome, certain skin diseases, aging, and certain inflammatory processes where the disease state is connected with the localized breakdown of protein by elastase could be treated by elastase inhibitors, such as the compounds of this invention. For example, degradation of fibronectin, an important biological substance, could be inhibited. McDonald, J. A., and D. G. Kelley, *J. Biol. Chem.*, 255, 8848 (1980). The compounds may also be useful in the treatment of other enzyme related diseases, such as fribrosis related to prolylhydroxylase, hypercholesterolemia related to HMG CoA reductase, and the like. This invention is not limited to these examples as one skilled in the art could readily apply these methods to any protease related disease or condition.

The method of the invention can be practiced in a variety of ways and the compounds can be administered in a number of dosage forms. A preferred method of delivery would be in such a manner so as to localize the action of the inhibitor. So, for example, in arthritis, the compounds could be injected directly into the affected joint, or for emphysema, the compounds could be inhaled using an aerosol or other appropriate spray. In any event, the compounds may be administered in any conventional manner. The compounds could be administered in oral unit dosage forms such as tablets, capsules, pills, powders or granules. They also may be administered rectally or vaginally in such forms as suppositories. They may be introduced in the forms of eyedrops, intraperitoneally, subcutaneously, or intramuscularly using forms known to the pharmaceutical art. For the treatment of inflammatory skin diseases, the compounds of the present invention may also be administered topically in the form of ointments, creams, gels or the like. Regardless of the route of administration selected, the compounds are formulated into pharmaceutically acceptable dosage forms by conventional methods known to the pharmaceutical art.

An effective but non-toxic quantity of the compound is employed in treatment. The dosage regimen for elastase inhibition by the compounds of this invention is selected in accordance with the variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ relatively low dosages at first, subsequently increasing the dose until a maximum response is obtained.

The compounds useful in practicing the method of this invention are prepared by methods illustrated in Charts A, B and C. Chart A illustrates two methods used to prepare compounds of Formula XIII from hydroxy- or alkoxy-substituted benzoic esters, Formula XI. In one method, compounds of Formula XI undergo Friedel-Crafts acylations with acyl halides in the presence of Lewis acids, giving compounds of Formula XIII directly. directly. Preferred conditions include reaction with an alkanoyl chloride, such as octadecanoyl chloride, in refluxing tetrahydrofuran containing aluminum chloride. In another method, compounds of Formula XI first react with acyl halides to form ester intermediates of Formula XII. Preferred conditions include reaction with an alkanoyl halide, such as octadecanoyl chloride, in tetrahydrofuran containing a tertiary amine base, such as triethylamine. The intermediates thus formed undergo Fries rearrangement in the presence of Lewis acids. Preferred conditions include refluxing 1,1,2,2-tetrachloroethane containing aluminum chloride or heating Formula XII and aluminum chloride without solvent.

Compounds of Formula XIII may further be modified to give other compounds of the invention. For example, ketones of Formula XIII may be converted to corresponding alcohols, Formula XIV, by reaction with activated hydride reducing agents. Preferred conditions include reaction with sodium borohydride in ethanol. Alcohols of Formula XIV may also be converted back to ketones, Formula XIII, by reaction with suitable oxidizing agents, such as manganese dioxide. Chart B illustrates other methods used to convert compounds of Formula XIV to additional compounds of this invention. Alcohols of Formula XIV may be dehydrated by heating in the presence of an acid catalyst, giving alkenes of Formula XXI. Preferred conditions include refluxing benzene or toluene containing p-toluenesulfonic acid. Alkenes of Formula XXI may be reduced to corresponding alkanes, Formula XXII. Preferred conditions include hydrogenation in an organic solvent, such as acetic acid, over a noble metal catalyst, such as palladium or rhodium.

Further modifications of the compounds described above can be effected by methods known to those skilled in the art. For example, the esters of Formula XXIII may be hydrolyzed to free acids of Formula XXIV. Preferred conditions include alkali metal hydroxides in water, followed by neutralization with a dilute mineral acid. Corresponding carboxylic acid salts (e.g., having a metal or other positively charged counter ion) may readily be prepared by methods known to those skilled in the art. Aryl hydroxyl groups of Formula XXV may be derivatized, for example, by conversion to alkyl ethers of Formula XXVI by reaction with alkyl halides or tosylates. Preferred conditions include heating at reflux in xylene containing potassium carbonate, with provisions to extract water with a Dean-Stark trap, followed by alkylation with alkyl tosylates.

Additonal methods for preparing the compounds of this invention will be apparent to those skilled in the art. For example, compounds can be prepared by methods utilizing Wittig reactions, Codogan, J. I. G., ed., *Organophosphorus Reagents in Organic Synthesis*, Academic Press (London, 1979), or aldol condensations, Nielson, *Organic Reactions*, 16, 1–444 (1968); Mukaiyama, T. *Organic Reactions*, 28, 203–331 (1982). Chart C illustrates the application of aldol condensation. Substituted acetophenones of Formula XXXI react with aldehydes under basic or acidic conditions to form hydroxyketones of Formula XXXII. Dehydration of compounds of Formula XXXII, using methods described above (See also Chart B), afford unsaturated ketones of Formula XXXIII. Hydrogenation of Formula XXXIII, using methods described above (See also Chart B), affords ketones of Formula XXXIV, which are homologous to corresponding ketones of Formula XIII (Chart A).

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples, temperatures are given in degrees celcius (°C.) and quantities of materials in grams and milliliters unless otherwise noted.

DESCRIPTION OF THE PREFERRED EMBODIMENTS

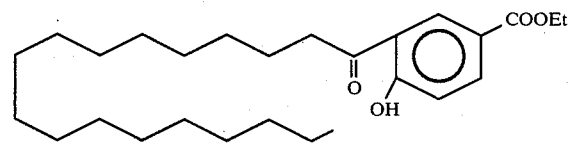

EXAMPLE 1

Ethyl 4-hydroxy-3-(1-oxooctadecyl)benzoate

Ethyl p-hydroxybenzoate (16.6 g), anhydrous aluminum chloride (28 g), and steroyl chloride (30.2 g) in 100 ml of tetrachloroethylane were stirred at room temperature overnight, then heated at reflux for 5 hours. The reaction mixture was added to ice/10% HCl with stirring and the layers allowed to separate. The aqueous phase was washed with 50 ml of dichloromethane and 50 ml of ethyl acetate. The organic phases were combined, dried over sodium sulfate, and then concentrated to dryness. The residue was chromatographed on silica gel to give the title compound, m.p. ca. 74° C.

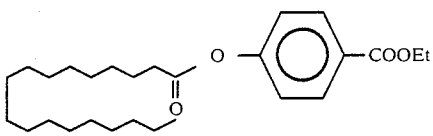

EXAMPLE 2

Ethyl 3-(octadecanoyloxy)benzoate

Steroyl chloride (10 g) was added to 5.5 g of ethyl p-hydroxybenzoate in 50 ml of tetrahydrofuran and stirred at room temperature for 4 hours. Under nitrogen, 4.6 ml of triethylamine was added with stirring in three equal portions. The mixture was stirred at room temperature overnight, then heated at reflux for one day. The solution was cooled to room temperature and solvent removed under $N_2$, and the products triturated with cyclohexane. The organic layers were combined, filtered and washed with water, 1N NaOH, 1N HCl, and water, then dried over sodium sulfate. Cyclohexane was removed under reduced pressure to give 12 g of product, m.p. ca. 57° C.

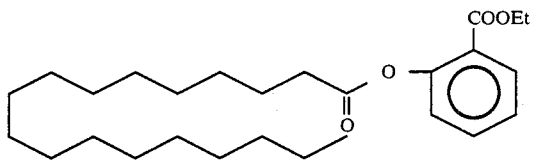

EXAMPLE 3

Ethyl 2-(octadecanoyloxy)benzoate

To a cold (+5° C.) solution of ethyl salicylate (0.136 moles) and stearoyl chloride (0.136 moles) in tetrahydrofuran (200 ml) was added triethylamine (0.136 moles) dropwise over 25 min. After refluxing for 20 hours, the solution was cooled to room temperature. Most of the tetrahydrofuran was removed with a $N_2$ stream during the cooling process. The residue was poured into ice/water (1500 ml), stirred for 1 hour, and a white solid removed by filtration. Washing the solid with water, followed by air drying gave 56 g of the title product, m.p. 50.5°-53.5° C.

Analysis calcd for $C_{27}H_{44}O_4$ (432.64): C, 74.96; H, 10.25. Found: C, 74.80; H, 10.51.

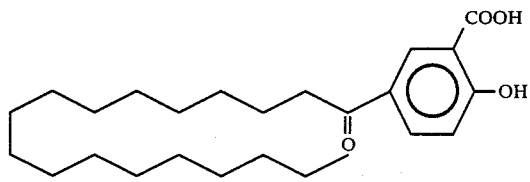

EXAMPLE 4

2-hydroxy-5-(1-oxooctadecyl)benzoic acid

Aluminum chloride (0.18 moles) was added in several portions to a solution of the compound from Example 3 (0.082 moles) in 1,1,2,2-tetrachloroethane (350 ml). The solution was stirred for 1 hour at room temperature and refluxed for 25 hours under a $N_2$ atmosphere, cooled to 5° C. and poured into 10% HCl (1000 ml). After standing 20 hours, methylene chloride (500 ml) was added and the layers separated. The organic layer was dried over sodium sulfate, filtered, and concentrated to dryness in a rotary evaporator. Hexane (500 ml) was added to the residue and left to stand 24 hours. The resultant solid was collected, then recrystallized from ethyl acetate. The dry solid product (10.2 g) was purified by chromatography on silica gel. Recrystallization from ethyl acetate gave the title compound (9.3 g), m.p. ca. 128°-134° C.

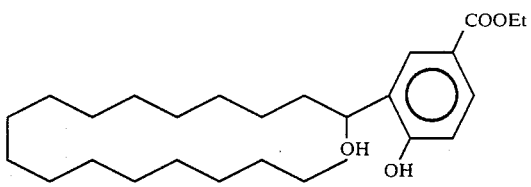

EXAMPLE 5

Ethyl 4-hydroxy-3-(1-hydroxyoctadecyl)benzoate

The title compound of Example 1 (1.0 g) was dissolved in 20 ml of absolute ethanol, and 0.1 g $NaBH_4$ was added with stirring under $N_2$ atmosphere. The reaction mixture was stirred for two hours, added to 1N HCl, and the mixture concentrated to dryness under reduced pressure to give a crystalline mass. This solid was extracted into ethyl acetate, and the extractants combined and washed with water, then dried over sodium sulfate. The solvent was removed under reduced pressure to give the title compound, m.p. ca. 75° C.

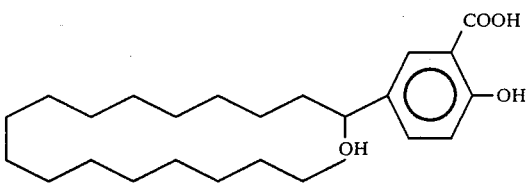

EXAMPLE 6

2-hydroxy-5-(1-hydroxyoctadecyl)benzoic acid

2-Hydroxy-5-(1-oxooctadecyl)benzoic acid (1.0 g) was added to 5 ml absolute ethanol, followed by 94 mg of $NaBH_4$.

The mixture was stirred at room temperature for 2 hours, then added to 10 ml of 0.1N HCl to give a solid. The solid was filtered, washed with 10 ml of water, dried in air and then at a pressure of 0.5 mm Hg at room temperature for about 65 hours to give the title compound, m.p. ca. 102° C.

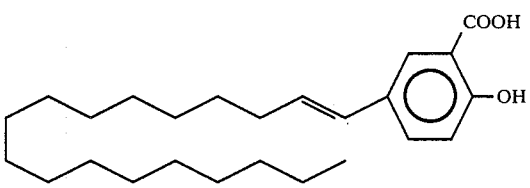

EXAMPLE 7

2-hydroxy-5-octadec-1-enylbenzoic acid

2-Hydroxy-5-(1-hydroxyoctadecyl)benzoic acid (100 mg) was dissolved in 20 ml of benzene and a trace of p-toluenesulfonic acid monohydrate added. The solution was refluxed for 10 minutes, then 10 ml of solvent was distilled. Reflux was continued for about 18 hours. Upon cooling to room temperature, the solution was extracted with 1% sodium bicarbonate solution and the solvent removed under a stream of nitrogen gas to give crystals. The material was recrystallized from methanol to give the title compound, m.p., ca. 95° C.

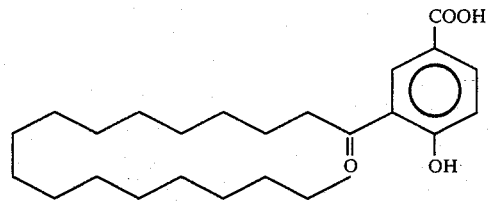

EXAMPLE 8

4-hydroxy-3-(1-oxooctadecyl)benzoic acid

The title compound of Example 1 (500 mg) was heated at reflux for 24 hours with 230 mg of lithium hydroxide monohydrate. The reaction mixture was cooled to room temperature, then added to 20 ml of 1N HCl with stirring, followed by the addition of 10 ml of water and 10 ml of ethyl acetate. The mixture was filtered and the solid recrystallized from dimethylformamide to give the title compound, m.p. ca. 170° C.

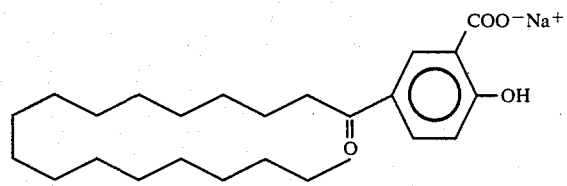

EXAMPLE 9

2-hydroxy-5-(1-oxooctadecyl)benzoic acid, monosodium salt

The title compound of Example 4 (500 mg) was dissolved in 10 ml of hot absolute ethanol and added to 123.6 ml of 0.01N sodium hydroxide with stirring. A solid separated but stirring was continued for an additional two hours. The mixture was filtered and the crystals dried overnight at room temperature and 0.5 mm Hg, then for four hours at 75° C. and 0.5 mm Hg.

Analysis calcd. for $C_{25}H_{39}O_4Na$: C, 70.39; H, 9.21; Na, 5.28. Found: C, 70.06; H, 9.21; Na, 5.14.

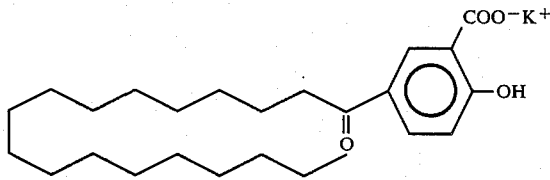

EXAMPLE 10

2-hydroxy-5-(1-oxooctadecyl)benzoic acid, monopotassium salt

A solution of the title product of Example 4 (4.95 mmole) and potassium acetate (4.95 mmole) in ethanol (40 ml) was heated at 65° C. for 2 hours. The volume was reduced to 10 ml under a nitrogen stream and the solution cooled in a refrigerator. The title compound was collected as a white solid, m.p. ca. 224°–230° C.

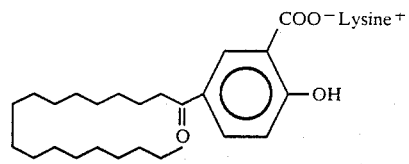

EXAMPLE 11

2-hydroxy-5-(1-oxooctadecyl)benzoic acid, lysine salt

A solution of the product of Example 4 (1.24 mmole) and L-lysine (1.24 mmole) in methanol (50 ml) was refluxed for 3 hours and stirred at 50° C. overnight. The solvent was removed under vacuum and the residue recrystallized from methanol to give 400 mg of the title compound.

Analysis calcd. for $C_{31}H_{54}N_2O_6$ (550.78): C, 67.60; H, 9.88; N, 5.09. Found: C, 67.24; H, 9.80; N, 4.91.

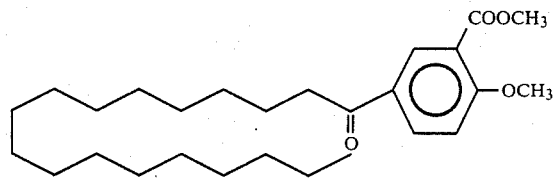

EXAMPLE 12

Methyl 2-methoxy-5-(1-oxooctadecyl)benzoate

Potassium carbonate (11.4 mmole) was added to a solution of the product of Example 4 (5.7 mmole) in 50 ml xylene, heated to reflux, and the water formed removed with a Dean-Stark trap. After 1 hour the Dean-Stark trap was drained. The solution was cooled to room temperature and methyl p-toluenesulfonate (17.1 mmole) added. The solution was heated to 70° C. for 20 hours, and refluxed for one hour to remove the water formed. After the white solid was filtered and discarded, the filtrate was concentrated under vacuum to a solid, which was was recrystallized from hot hexane, to give the title compound (1.6 g), m.p. ca. 73°–74° C.

Analysis calcd. for $C_{27}H_{44}O_4$ (432.62): C, 74.95; H, 10.25. Found: C, 75.19; H, 10.49.

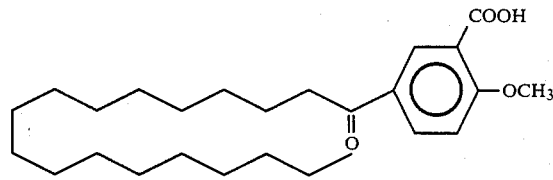

EXAMPLE 13

2-methoxy-5-(1-oxooctadecyl)benzoic acid

The product of Example 12 (3.47 mmole) was added to 75 ml methanol and 10 ml hot water. Lithium hydroxide (1.0 g) was added and the mixture stirred overnight at 45° C. The solvent was removed on a rotary evaporator and 1N HCl (100 ml) and $CH_2Cl_2$ (100 ml) were added to the residue. The layers were separated and the organic layer washed with water. The organic solution was dried with sodium sulfate, filtered, and concentrated to a solid. The title compound, m.p. 194°-6°, was purified by column chromatography.

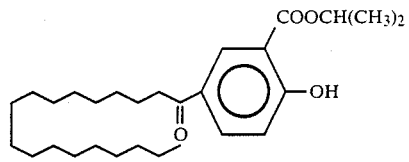

EXAMPLE 14

1-methylethyl 2-hydroxy-5-(1-oxooctadecyl)benzoate

A solution of the title product of Example 4 (6.2 mmole) and sulfuric acid (0.5 ml) in 120 ml of isopropyl alcohol (100 ml) was heated at 45° C. for 12 days, refluxed for 36 hours, and concentrated on a rotary evaporator to an oil. The oil was dissolved in methylene chloride, washed with water, dried over sodium sulfate, filtered, and concentrated under vacuum to give the title compound, m.p. 72°-73° C.

Analysis calcd. for $C_{28}H_{46}O_4$ (446.67): C, 75.29; H, 10.38. Found: C, 75.26; H, 10.30.

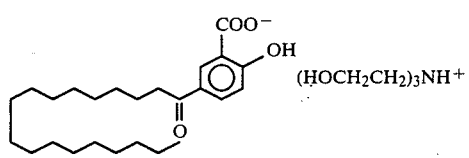

EXAMPLE 15

2-hydroxy-5-(1-oxooctadecyl)benzoic acid, tris(2-hydroxyethyl)amine salt

The title compound, m.p. ca. 84°, was prepared by the method of Example 10 using 500 mg of the compound of Example 4 and 184 mg of triethanolamine. The crude product was purified by crystallization from ethanol.

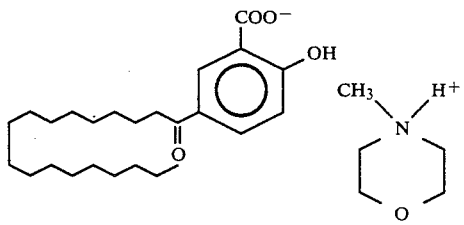

EXAMPLE 16

2-hydroxy-5-(1-oxooctadecyl)benzoic acid, N-methylmorpholine salt

The title compound, m.p. ca. 98°, was prepared by the method of Example 10 using 500 mg of the compound of Example 4 and 125 mg of N-methylmorpholine. The crude product was purified by crystallization from ethanol.

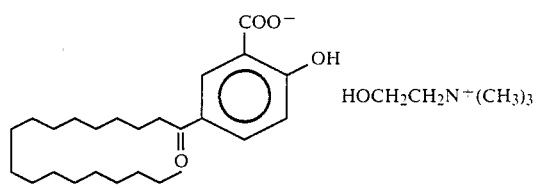

EXAMPLE 17

2-hydroxy-5-(1-oxooctadecyl)benzoic acid, 2-hydroxy-N,N,N-trimethyl ethanaminium salt The title compound was prepared by the method of Example 10 using 1.0 g of the compound of Example 4 and 630 mg cholinechloride. After removal of the resultant potassium chloride precipitate, the crude product was purified by crystallization from ethanol.

Analysis calcd. for $C_{30}H_{53}NO_5$: $\frac{1}{2}H_2O$: C, 69.73; H, 10.53; N, 2.71. Found: C, 69.45; H, 10.49; N, 3.08

EXAMPLE 18

The compound 2-hydroxy-5-(1-oxooctadecyl)benzoic acid, monopotassium salt was screened in the collagen-induced rat arthritis model described above.

The test compound retarded the progression of the arthritis when assessed by inflammatory swelling at the lesion site. Results were statistically significant (P=0.001).

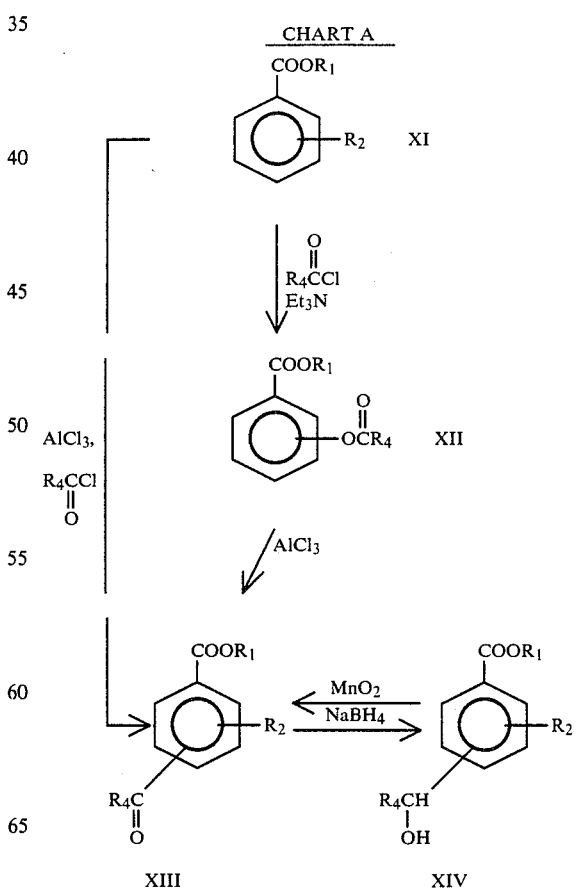

CHART B

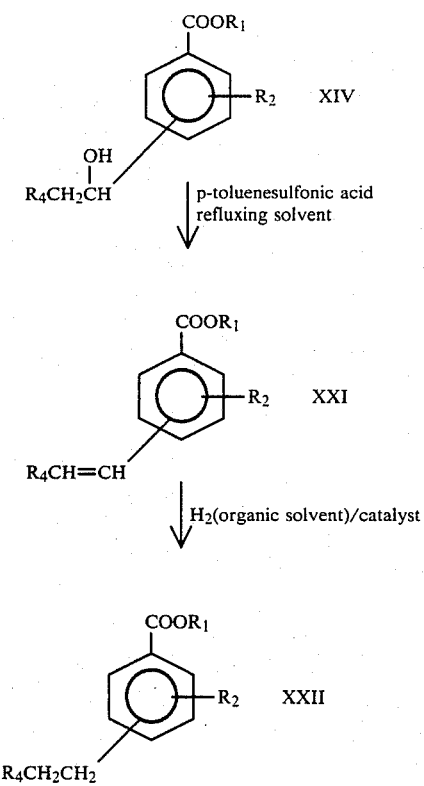

CHART C

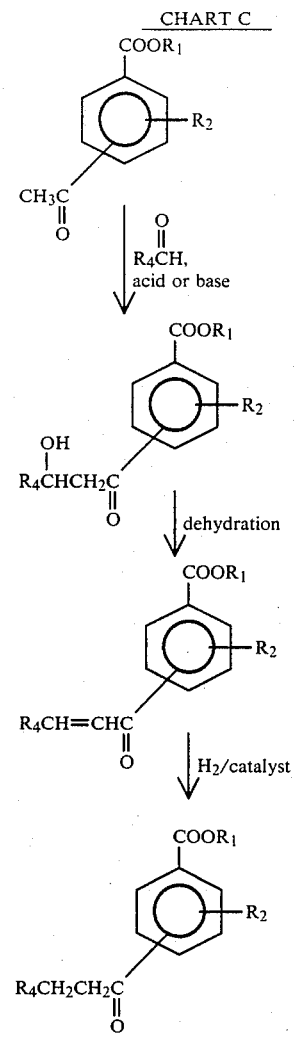

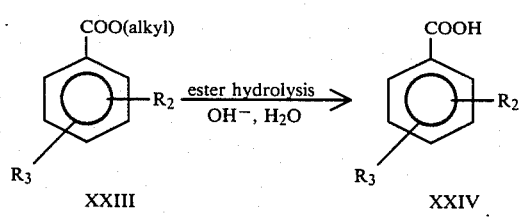

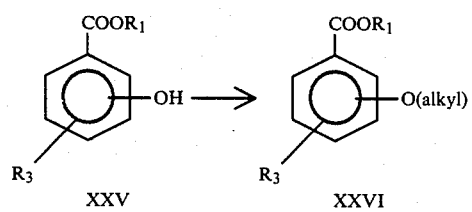

We claim:
1. Compounds of the formula:

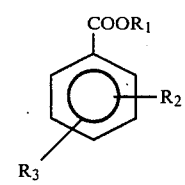

wherein $R_1$ is:
(a) hydrogen; or
(b) alkyl of 1 to 6 carbon atoms, inclusive;
wherein $R_2$ is:
(a) hydroxy; or
(b) alkoxy of 1 to 6 carbon atoms, inclusive;
wherein $R_3$ is $-CH=CHR_4$
wherein $R_4$ is alkyl of 13 to 25 carbon atoms inclusive or the pharmacologically acceptable addition salts thereof.

2. A compound according to claim 1 wherein the compound is 2-hydroxy-5-octadec-1-enylbenzoic acid.

* * * * *